US00PP17718P2

(12) United States Plant Patent
Evison et al.

(10) Patent No.: US PP17,718 P2
(45) Date of Patent: May 8, 2007

(54) ***CLEMATIS* VARIETY 'EVIPO004'**

(50) Latin Name: *Clematis viticella*
Varietal Denomination: EVIpo004

(75) Inventors: Raymond J. Evison, Guernsey (GB); Mogens N. Olesen, Fredensborg (DK)

(73) Assignees: Poulsen Roser A/S, Fredensborg (DK); Raymond J. Evison, Limited, Guernsey (GB)

( * ) Notice: Subject to any disclaimer, the term of this patent is extended or adjusted under 35 U.S.C. 154(b) by 1125 days.

(21) Appl. No.: 10/355,395

(22) Filed: Jan. 31, 2003

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell

(57) ABSTRACT

A new *Clematis* cultivar which is well suited to garden use. With a tall growth habit, profuse, nodding violet flowers, and continuous summer flowering. The variety successfully propagates from softwood cuttings and is suitable for ornamental use in outdoor settings in a variety of climatic conditions. This new and distinct variety has shown to be uniform and stable in the resulting generations from asexual propagation.

1 Drawing Sheet

SUMMARY OF THE INVENTION/DISCOVERY

Botanical classification: Genus: *Clematis.* Subgenus: *flammula.* Species: *viticella.*

Variety denomination: 'EVIpo004'.

Commercial: Late-flowering cultivar.

The present invention constitutes a new and distinct variety of *Clematis* which originated from chance pollination of the female parent 'EVIpure', unpatented, and the male parent, an unknown seedling. The resulting plant is named 'EVIpo004.'

The new variety may be distinguished from its seed parent, 'EVIpure', by the following combination of characteristics:

1. Whereas 'EVIpure' has an average flower diameter of 120 mm, 'EVIpo004' has an average flower diameter of 100 mm.
2. Whereas 'EVIpure' has tepals which are mainly White Group 155C, 'EVpo004' has tepals which are Violet Group 86A.

The objective of the hybridization of this *Clematis* variety for commercial nursery culture was to create a new and distinct variety with unique qualities, such as:

1. A tall growth habit;
2. A profusion of semi-nodding violet flowers;
3. Summer flowering;
4. Well suited to garden use.

These qualities required improvement in *Clematis* varieties that were in commercial cultivation and the objectives have been substantially achieved in the new variety, as evidenced by the unique combination of characteristics that are present in 'EVIpo004' which distinguish it from all other varieties of which we are aware.

After the chance pollination occurred, seeds were collected from the female plant 'EVIpure'. The seeds were germinated and evaluations were conducted of the resulting *Clematis* seedling plants in a controlled environment. 'EVIpo004' was selected by Raymond J. Evison and Mogens N. Olesen in their *Clematis* development program in Domarie Vineries Les Sauvagees, St. Sampsons, Guernsey, Channel Islands, United Kingdom in July, 1997.

Asexual reproduction of 'EVIpo004' by cuttings was first done by Raymond J. Evison and Mogens N. Olesen in Domarie Vineries Les Sauvagees, St. Sampsons, Guernsey, Channel Islands, United Kingdom in August, 1997. This initial and subsequent propagations have demonstrated that the characteristics of 'EVIpo004' are true to type and are transmitted from one generation to the next.

BRIEF DESCRIPTION OF THE DRAWING

The accompanying color illustration show as true as is reasonably possible to obtain in color photographs of this type:

FIG. 1: Side view of various stages of flower development, including the pedicel, flower buds, and attachment of leaves.

FIG. 2: Open bloom, lower side.

FIG. 3: Open Bloom, upper side, including filaments.

FIG. 4: Mature foliage.

FIG. 5: Juvenile foliage.

DETAILED DESCRIPTION OF THE VARIETY

The following is a detailed description of 'EVIpo004', as observed in its growth throughout the flowering period in glasshouses at Domarie Vineries Les Sauvagees, St. Sampsons, Guernsey, Channel Islands, United Kingdom. The observed plants are 2 years of age, grown in 2 liter sized containers, in an unheated glasshouse. Certain phenotypical characteristics of the variety may vary under different environmental, cultural, agronomic, seasonal, and climatic conditions. Color references are made using The Royal Horticultural Society (London, England) Colour Chart, 2001. For a comparison, the nearest existing *Clematis* variety is 'Durandii', a non-patented *Clematis* variety. Chart 1 details several physical characteristics of 'EVIpo004' and the comparison variety.

CHART 1

| | 'EVIpo004' | 'Durandii' |
|---|---|---|
| Flower Color | Violet Group 86A. | Violet Group 89C. |
| Growth Height | 2.5 to 3 M. | 1.75 to 3 M. |

Female parent: 'EVIpure'.
Male parent: Unknown.

FLOWER AND FLOWER BUD

Blooming habit: Recurrent.
Flowering period: June, July, August, September.
Flower bud:
*Size.*—20 to 35 mm in length. 10 to 12 mm in diameter.
*Bud form.*—Ovoid.
*Bud color.*—Violet Blue 92C at ¼ opening.
*Tepals.*—Violet Group 86A.
*Peduncle.*—Surface: Smooth. Length: 100 to 120 mm average length. Color: Green Group 137A. Strength: Somewhat nodding.
*Receptacle.*—No receptacle observed.
*Borne.*—Compound cyme.
Flower bloom:
*Size.*—100 mm diameter on average. 30 mm in depth.
*Form.*—Concave, with straight tepals.
*Color.*—Upon opening: Upper surface: Violet Group 86A. Lower surface: Violet Blue Group 90A. After opening: Upper surface: Violet Group 86A. Lower surface: Violet Blue Group 90B retained with in the bisecting vein of the tepal. Intonations of Violet Blue Group 90D dominate the marginal zones, and Violet Group 86A at basal zones.
Fragrance: None.
*Lasting quality on plant.*—Flowers persist for 10–14 days.
Tepals:
*Tepal count.*—Single: Four tepals.
*Shape.*—Elliptic.
*Cross section.*—Sightly cupped.
*Undulation of margin.*—Weak. Undulation depth is 5 to 10 mm, occurring 1 to 2 times in each tepal length.
*Tepal margin.*—Entire.
*Tepal apex.*—Narrowly acute.
*Recurvature of tip.*—Slightly recurved.
*Persistence.*—Tepals drop off cleanly.
*Arrangement.*—Tepals are arranged regularly.
Reproductive organs:
*Pistils.*—Quantity: 50.
*Pollen.*—Abundance: Scant. Color: Greyed-Orange Group 166A.
*Anthers.*—Size: Small. Color: Yellow Green Group 144A.
*Arrangement.*—Regular.
*Filaments.*—Color: Violet Group 83A.
*Stigmas.*—Stigmas not visible.
*Styles.*—Color: Yellow-Green Group 144A.
*Seed.*—The plant does not normally produce seed.

PLANT

Plant form: Upright.
Plant growth: Vigorous.
Height: Seasons growth attains meters 2.5 to 3 meters.
Width: 1 to 2 meters.
Hardiness: Trials to date show the variety hardy in USDA Zones 4–9.
Stems:
*Color.*—Young wood: Green Group 137D with intonations of Red Purple Group N70A. Older wood: Greyed Orange Group 165C.
*Internodes.*—Cylindrical. Length 100 mm. Clasping: No clasping.
*Bark.*—Young wood: Smooth. Older wood: Rough.
Plant foliage: Deciduous. Occasionally simple. Normally 5 leaflets per compound leaf.
*Leaf.*—Size: 30 to 60 mm long. Abundance: Average. Color: Upper side: Green Group 139A. Lower side: Green Group 137C.
Plant leaves and leaflets:
*Stipules.*—Absent.
*Petiole.*—Size: 20 mm in length on compound leaves; none on simple leaves. Color: Green Group 137C with intonations of Red Purple Group 70A.
*Leaf size.*—Terminal Leaflet Length: 30 to 60 mm. Terminal Leaflet Width: 20 to 30 mm. Compound Leaf Length: 120 mm. Compound Leaf Width: 90 mm. Underneath: Without prickles.
*Leaf edge.*—Terminal leaflet margin is entire.
*Shape.*—Base of leaflet: Acute to oblique. Apex of leaflet: Acute. Overall shape: Ovate to lanceolate. Margin of leaflet: Varying from entire to occasional acute edges.
*Texture.*—Smooth. Upper side: Glabrous. Lower side: Glabrous.
*Surface.*—Matte finish.
Disease resistance: Subject to any disease that normally attacks the species, however the variety is more tolerant to Mildew than other *clematis* known to us.

It is claimed:

1. A new and distinct variety of *clematis* plant, substantially as herein shown and described, as a distinct and novel *clematis* variety due to its abundant, violet flowers, with good lastingness, attractive long lasting foliage and compact grwth, year round flowering under glasshouse conditions, suitability for production from softwood cuttings in pots, durable flowers, and foliage which makes the variety suitable for distribution in the floral industry.

* * * * *

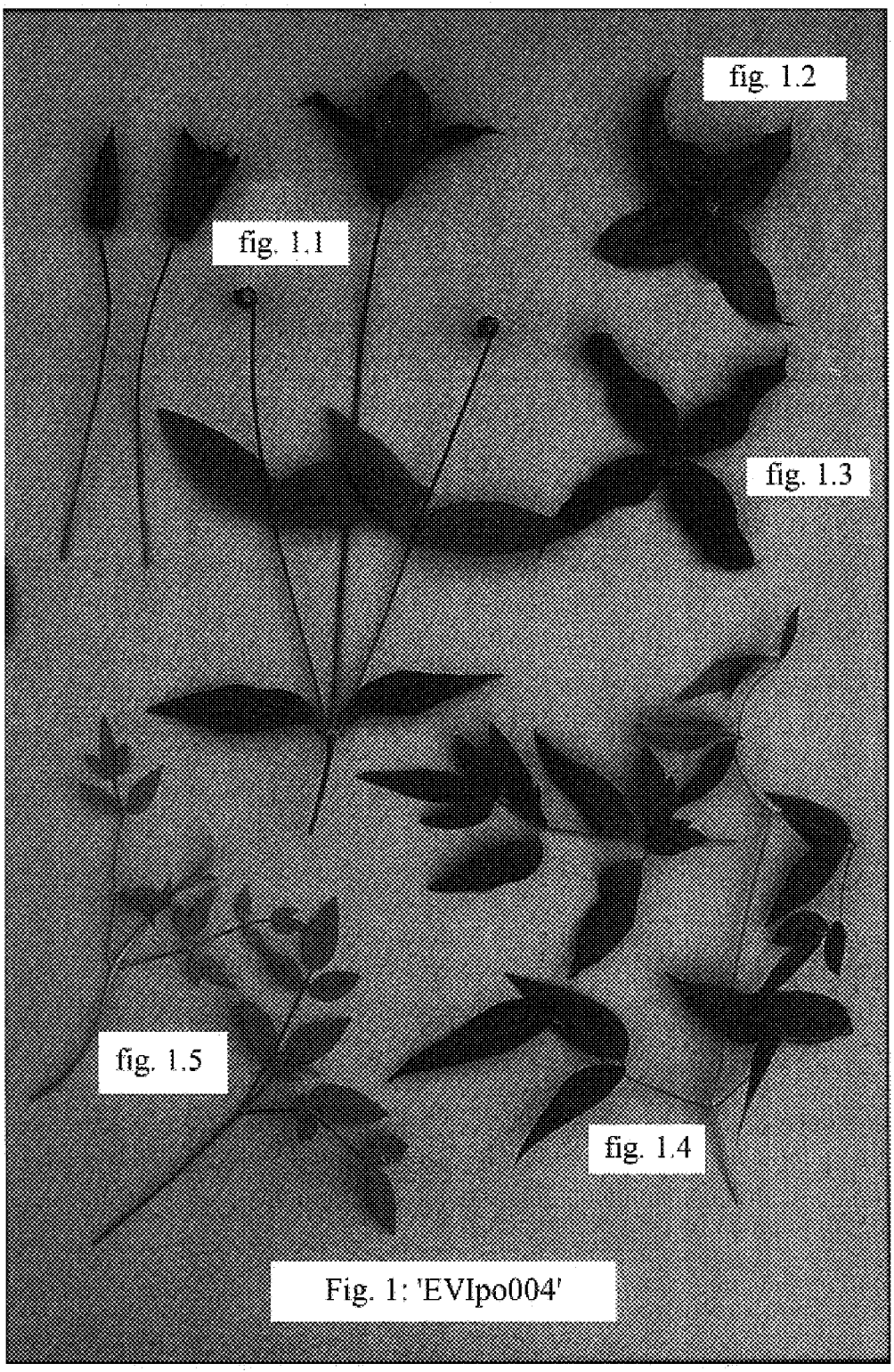
Fig. 1: 'EVIpo004'